United States Patent
Camaggi et al.

[11] Patent Number: 5,464,836
[45] Date of Patent: Nov. 7, 1995

[54] BENZOPHENONES HAVING AN ANTIFUNGAL ACTIVITY

[75] Inventors: Giovanni Camaggi, Novara; Lucio Filippini, San Donato Milanese; Marilena Gusmeroli, Monza; Raul Riva, Novara; Carlo Garavaglia, Cuggiono; Luigi Mirenna, Milan, all of Italy

[73] Assignee: Ministero Dell'Universita' E Della Ricerca Scientifica E Tecnologica, Rome, Italy

[21] Appl. No.: 131,880

[22] Filed: Oct. 5, 1993

Related U.S. Application Data

[63] Continuation of Ser. No. 904,554, Jun. 26, 1992, abandoned.

[30] Foreign Application Priority Data

Jul. 1, 1991 [IT] Italy ................... MI91A1812

[51] Int. Cl.$^6$ ................. A61K 31/535; C07D 265/30; C07C 211/27
[52] U.S. Cl. .................. 514/239.2; 514/231.2; 514/648; 514/227.5; 514/315; 544/59; 544/174; 544/175; 546/237; 564/323; 564/324
[58] Field of Search ............ 544/59, 174, 175; 546/237; 564/323, 324; 514/227.5, 315, 239.2, 239.5, 648, 231.2

[56] References Cited

U.S. PATENT DOCUMENTS

| | | |
|---|---|---|
| 3,117,059 | 1/1964 | Rubinstein . |
| 3,123,643 | 3/1964 | Palopoli et al. . |
| 3,272,841 | 9/1966 | De Wald . |
| 3,708,482 | 1/1973 | Lauria et al. . |
| 3,867,381 | 2/1975 | Houlihan .................. 544/175 |
| 4,216,326 | 8/1980 | Zenitz ..................... 544/174 |
| 5,106,878 | 4/1992 | Guerry et al. . |
| 5,137,920 | 8/1992 | Guerry et al. . |

FOREIGN PATENT DOCUMENTS

| | | |
|---|---|---|
| 0108592 | 5/1984 | European Pat. Off. . |
| 410359 | 1/1991 | European Pat. Off. ........... 564/324 |
| 2212141 | 7/1974 | France . |
| 1115158 | 5/1968 | United Kingdom ............... 564/324 |

Primary Examiner—Johann Richter
Assistant Examiner—Jacqueline Haley
Attorney, Agent, or Firm—Oblon, Spivak, McClelland, Maier & Neustadt

[57] ABSTRACT

A description follows of benzophenones having an antifungal activity and corresponding to the general formula (I):

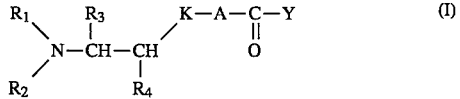

wherein:

$R_1$ and $R_2$, the same or different, represent $C_1$–$C_6$ alkyl groups, $C_7$–$C_{10}$ arylalkyl groups; or $R_1$ and $R_2$, considered jointly with N, represent a $C_3$–$C_8$ heterocyclic group or a $C_2$–$C_7$ heterocyclic group containing a second hetero-atom selected from O and S, said heterocyclic groups being optionally subsituted with one or more $C_1$–$C_4$ alkyl groups;

$R_3$ and $R_4$, the same or different, represent H atoms, $C_1$–$C_3$ alkyl groups;

K represents an oxygen atom or methylene;

A represents a benzene group, optionally sustituted with one or more halogen atoms, $C_1$–$C_4$ alkyl or haloalkyl groups, $C_1$–$C_4$ alkoxylics, $C_1$–$C_4$ haloalkoxylics;

Y represents a $C_6$–$C_{10}$ aryl group; said group may be optionally substituted with one or more halogen atomos, $C_1$–$C_4$ alkyl or haloalkyl groups, $C_1$–$C_4$ alkoxylics, $C_1$–$C_4$ haloalkoxylics.

5 Claims, No Drawings

BENZOPHENONES HAVING AN ANTIFUNGAL ACTIVITY

This application is a continuation of application Ser. No. 07/904,554, filed on 26 Jun. 1992, now abandoned.

The present invention relates to benzophenones having a high antifungal activity, to the process for their preparation and to their relative use as fungicides in the field of agriculture.

In particular the present invention relates to compounds corresponding to the general formula (I):

$$\begin{array}{c} R_1 \\ \phantom{R}\diagdown \\ R_2 \end{array} N-CH-CH \begin{array}{c} R_3 \\ | \\ R_4 \end{array} \begin{array}{c} K-A-C-Y \\ \phantom{K}\phantom{A}\phantom{C} \| \\ \phantom{K}\phantom{A}\phantom{C} O \end{array} \quad (I)$$

wherein:

$R_1$ and $R_2$, the same or different, represent $C_1$–$C_6$ alkyl groups, $C_7$–$C_{10}$ arylalkyl groups; or $R_1$ and $R_2$, considered jointly with N, represent a $C_3$–$C_8$-heterocyclic group or $C_2$–$C_7$-heterocyclic group containing a second hetero-atom selected from O and S, said heterocyclic groups being optionally substituted with one or more $C_1$–$C_4$ alkyl groups;

$R_3$ and $R_4$, the same or different, represent H atoms, $C_1$–$C_3$ alkyl groups;

K represents an oxygen atom or methylene;

A represents a benzene group, optionally substituted with one or more halogen atoms, $C_1$–$C_4$ alkyl or haloalkyl groups, $C_1$–$C_4$ alkoxylic groups, $C_1$–$C_4$ haloalkoxylic groups;

Y represents a $C_6$–$C_{10}$ aryl group; said group may be optionally substituted with one or more halogen atom, $C_1$–$C_4$ alkyl or haloalkyl groups, $C_1$–$C_4$ alkoxylic groups, $C_1$–$C_4$ haloalkoxylic groups.

The compounds corresponding to formula (I) have at least one asymmetrical centre: the present invention includes the synthesis and use of enantiomorphically or diastereosomerically pure compounds or mixtures of these in any ratio.

In the description of the invention, halogens refer to F, Cl, Br, I atoms.

Examples of aryl groups are phenylene, naphthyl and similar higher groups.

Examples of arylalkyl groups are benzyl and 3-phenylpropyl.

Examples of groups $$\begin{array}{c} R_1 \\ \phantom{R}\diagdown \\ \phantom{R}\phantom{\diagdown} N-, \\ \phantom{R}\diagup \\ R_2 \end{array}$$

when taken together, they represent a $C_3$–$C_8$ group, or a $C_2$–$C_7$ hetero-cyclic group, defined above, are groups derived from morpholine, piperidine, thiomorpholine, etc., also substituted as defined above.

The present invention also relates to:

the salts of compounds corresponding to general formula (I) derived from an inorganic acid such as a halogenide, for example, iodide, bromide; sulphuric acid, nitric acid, thiocyanic acid and phosphoric acid; or from an organic acid such as acetic acid, propanoic acid, ethane dioic acid, propane dioic acid, benzoic acid, salicylic acid, saccharin, methansulphonic acid, 4-methylbenzenesulphonic acid, etc., in accordance with the known techniques;

metallic complex compounds obtained by complexion reaction between the derivatives of type (I) with an organic or inorganic metal salt such as a halide, nitrate, sulphate, phosphate, for example, of copper, manganese, zinc or iron, in accordance with the known techniques.

The compounds corresponding to formula (I) can be prepared by means of different synthesis schemes.

A preferred method may be schematically represented as follows:

$$R_3-\overset{\overset{\displaystyle O}{\|}}{C}\diagdown_{\underset{R_4}{\overset{|}{CH}}}\diagup K-A-\overset{\overset{\displaystyle O}{\|}}{C}-Y + H-N\diagdown_{R_2}^{R_1} \xrightarrow{NaBH_3-CN}$$
(II)  (III)

$$\begin{array}{c} R_1 \\ \phantom{R}\diagdown \\ R_2 \end{array} N-CH-CH \begin{array}{c} R_3 \\ | \\ R_4 \end{array} \begin{array}{c} K-A-C-Y \\ \phantom{K}\phantom{A}\phantom{C} \| \\ \phantom{K}\phantom{A}\phantom{C} O \end{array} \quad (I)$$

More clearly, the carbonyl (II) is reacted with amine (III), and the cyanosodiumboron hydride in a protic solvent (methanol, ethanol) at a temperature ranging from –5° to 25° C., to obtain compound (I). (Cfr. Organic Synthesis, Vol. 52, page 124).

In the preparation scheme, the symbols $R_1$, $R_2$, $R_3$, $R_4$, K, A, Y have the meaning already defined.

The salts and/or complex compounds can be prepared from products (I) following the known methods.

The amines are produced commercially or can be easily obtained by synthesis (cfr: J. March, "Advanced Organic Chemistry", II edition, Int St Edition, page 357).

The carbonyl compounds (II) can generally be produced and prepared using the known techniques.

When K is a methylene, a preferred method may be schematically represented as follows:

$$R_3-\underset{\underset{R_4}{|}}{CH}-\underset{\underset{H}{|}}{C}=\overset{H}{\underset{|}{C}} + Z-A-\overset{\overset{\displaystyle O}{\|}}{C}-Y \xrightarrow[base]{catalyst} (II)$$
(IV)      (V)

More specifically, the allyl alcohol (IV) is reacted with benzophenone (V), wherein Z has the meaning of a halogen (Br, I) or an activated ester (trifluoromethansulphonic), in the presence of a Palladium salt (II) (Pd chloride, Pd acetate), or in the presence of metallic Palladium supported, for example, on carbon or inorganic salts (sodium bicarbonate, sodium carbonate). These forms of metallic Palladium are often more effective if prepared "in situ". The reaction is often carried out in the presence of an organic base (triethylamine, tributylamine) or inorganic base (sodium bicarbonate, potassium carbonate), in a protic solvent (water, ethanol) or bipolar aprotic solvent (N,N-dimethylformamide, N-methylpyrrolidone), at a temperature ranging from 0° C. to the boiling point of the solvent. It could be advantageous to add phosphines such as triphenylphosphine and triorthotolylphosphine (cfr. JOC 41, 1206, 1976).

In the preparation scheme (II), $R_3$, $R_4$, A, Y have the meanings already defined.

The alcohols (IV) and the benzophenones (V) can generally be prepared using the known methods.

The compounds corresponding to general formula (I) are highly active in inhibiting the growth of various species of pathogenous fungi which attack cultivations of useful plants.

They have both a preventive and curative activity when applied to useful plants or parts of these, such as leaves, and are particularly effective in preventing diseases caused by obligate pathogenous fungi, such as, for example, those belonging to the Helminthosporium genera.

Examples of plant diseases which can be fought with the compounds of the present invention are:

*Erysiphe graminis* on cereals

*Sphaeroteca fuliginea* on cucurbitaceae (for example, cucumber)

Puccinia, on cereals

Septoria on cereals

Helminthosporium on cereals

Rhynchosporium on cereals

*Podosphaera leucotricha* on apple-trees

*Uncinula necator* on vines

*Venturia inaequalis* on apple-trees

*Pyricularia oryzae* on rice

*Botrytis cinerea*

Fusarium on cereals and other diseases.

For practical use in agriculture, it is often useful to prepare fungicidal compositions containing one or more of the compounds corresponding to formula (I) as an active substance.

These compositions may be applied to any part of the plant, for example, leaves, stems, branches and roots, or on the seeds themselves, before sowing, or even in the soil where the plant grows. Compositions in the form of dry powders, wettable powders, emulsionable concentrates, pastes, granulates, solutions, suspensions etc. may be used: the choice of the kind of composition will depend on the specific use. The compositions are prepared according to the known techniques, such as diluting or dissolving the active substance with a solvent medium and/or solid diluent, optionally in the presence of surface-active agents. The following may be used as solid diluents, or supports: silica, kaolin, bentonite, talc, infusorial earth, dolomite, calcium carbonate, magnesia, chalk, clays, synthetic silicates, attapulgite, sepiolite. As liquid diluents, apart from water naturally, various kinds of solvents may be used, for example aromatics (benzene, xylenes, or mixtures of alkylbenzenes), chloroaromatics (chlorobenzene), paraffins (fractions of petroleum), alcohols (methanol, propanol, butanol), amines, amides (dimethylformamide), ketones (cyclohexanone, acetophenone, isophorone, ethyl amyl ketone), esters (isobutyl acetate). As surface-active agents: sodium, calcium or triethanolamine salts of alkylsulphates, alkylsulphonates, alkyl-arylsulphonates, polyethoxylated alkylphenols, fatty alcohols condensed with ethylene oxide, polyoxyethylated fatty acids, esters of polyoxyethylated sorbitol, polyoxyethalate fats, ligninsulphonates. The compositions may also contain special additives for specific purposes, for example, adhesive agents such as arabic rubber, polyvinyl alcohol, polyvinyl pyrrolidone.

If required, it is also possible to add to the compositions of the present invention other compatible active substances such as fungicides, agrochemicals, phyto-regulators, weed-killers, insecticides, fertilizers.

The concentration of the active substance in the above compositions may vary within a wide range, depending on the active compound, the cultivation, pathogen, environmental conditions and type of formulation used. In general the concentration of the active substance varies from 0.1 to 95, preferably from 0.5 to 90% by weight.

The following examples illustrate the invention.

EXAMPLE 1

Synthesis of4-[3-(3-benzoylphenyl)-2-methylpropyl]-2,6-dimethylmorpholine (Compound No.1).

0.7 g of 2,6-dimethylmorpholine hydrochloride, a mixture of cis-trans isomers, are dissolved in 8 cc of methanol. 0.069 g of potassium hydroxide and 1 g of 3-(3-benzoylphenyl)-2-methylpropanal are added. After 15 minutes a solution of 0.084 g of sodium cyanoboron hydride in 1 cc of methanol are added dropwise and after a further 30 minutes 0.27 g of potassium hydrate in powder form are added. The mixture is filtered on celite and the solvent evaporated at reduced pressure. The raw product is purified by silica gel chromatography, with hexane/ethyl acetate=9/1 as eluant, to obtain 0.8 g of compound 1, cis isomer.

Analysis

NMR (60 Mhz) in $COCl_3$:

=8.0–7.2 (m, 9H)

3.5 (m, 2H)

3.0–1.4 (m, 9H)

1.3–0.8 (m, 9H)

EXAMPLE 2

Synthesis of 3-(3-benzoylphenyl)-2-methylpropanal.

0.085 g of palladium chloride, 0.254 g of triphenylphosphine and 16.9 g of sodium bicarbonate are dispersed in 35 cc of N-methyl-pyrrolidone. Hydrogen is introduced into the reaction flask for 30', under vigorous stirring. The hydrogen is removed with repeated washing with nitrogen and 10 g of 3-bromobenzophenone and 3.75 g of 2-methyl-prop- 2-en-1-ol are then added.

The mixture is heated to 120° C. for 0.5 hours.

At the end of the reaction the solution is filtered on celite, 80 cc of water are added and extraction takes place with diethyl ether (50 cc twice). The organic phase, which evaporates at reduced pressure, is anhydrified. The raw product is purified by silica gel chromatography, with hexane/ethyl acetate =9/1 as eluant, to obtain 8.9 g of the required product.

Analysis

NMR (60 Mhz) in $COCl_3$

=9.8 (s, 1H)

8.0–7.0 (m, 9H)

3.2–2.6 (m, 3H)

1.2 (d, 3H)

1.3–0.8 (m, 9H)

EXAMPLE 3

Using the same procedure described in Example 1, starting from the corresponding reagents, compounds 2–9 were synthesized and the NMR analytic characteristics are given below:

Compound 2

4-[3-(3-(4-chlorobenzoyl)phenyl)-2-methylpropyl]-2,6-dimethylmorpholine (cis isomer).

NMR (60 Mhz) in COCl$_3$:
=7.9–7.2 (m, 9H)
3.5 (m, 2H)
3.0–1.4 (m, 9H)
1.3 - 0.8 (m, 9H)

Compound 3

4-[3-(3-(4-fluorobenzoyl)phenyl)-2-methylpropyl]-2,6-dimethylmorpholine (cis isomer).

NMR (60 Mhz) in COCl$_3$:
=8.0–6.9 (m, 9H)
3.5 (m, 2H)
2.9–1.4 (m, 9H)
1.2–0.7 (m, 9H)

Compound 4

4-[3-(3-benzoylphenyl)-2-methyl-3 -3 -oxapropyl ]-2,6-dimethylmorpholine (cis isomer).

NMR (60 Mhz ) in COCl$_3$:
=8.0–7.0 (m, 9H)
4.6 (m, 1H)
3.6 (m, 2H)
2.5 (m, 4H)
1.8 (m, 2H)
1.3 (m, 3H)
1.1 (m, 6H)

Compound 5

N-[3-(3-benzoylphenyl)-2-methyl-3-oxapropyl]-N-benzyl-N-methylamine.

NMR (60 Mhz ) in COCl$_3$
=8.0–7.0 (m, 9H)
4.6 (m, 1H)
3.6 ( s, 2H)
2.7 (m, 2H)
2.3 (s, 3H)
1.35 (d, 3H)

Compound 6

4- [3- (3- (3,4 dimethoxybenzoyl)phenyl )-2-methylpropyl ] -2,6 dimethylmorpholine (cis isomer).

NMR (60 Mhz ) in COCl$_3$
=7.5–6.7 (m, 7H)
3.8 (s, 6H)
3.5 (m, 2H)
1.4–2.8 (m, 9H)
0.6–1.2 (m, 9H)

Compound 7

N- [3 - (3 -benzoylphenyl )-2-methylpropyl]-N-methyl-N- (3-phenylpropyl)amine.

NMR (60 Mhz ) in COCl$_3$
= 7.8 - 7.1 (m, 14H)
1.5–2.75 (m, 11H)
2.1 (s, 3H)
0.9 (d, 3H)

Compound 8

N-[3 -(3-benzoylphenyl)-2-methylpropyl]-N-methyl-N-benzyl amine.

NMR (60 Mhz ) in COCl$_3$
=7.9–7.1 (m, 14H)
3.5 (s, 2H)
3.1–1.6 (m, 5H)
2.1 (s, 3H)
0.9 (d, 3H)

Compound 9

N- [3- (3-benzoylphenyl)-2-methylpropyl] -N, N-dipropyl amine.

NMR (60 Mhz ) in COCl$_3$
=7.8–6.8 (m, 9H)
3.1–1.0 (m, 13H)
0.8 (m, 9H)

EXAMPLE 3

Determination of the preventive fungicidal activity on *Helminthosporium teres*.

Barley leaves cv. Arna, cultivated in a vase in a conditioned environment, were treated by spraying both sides with the products being tested (compounds 1 and 2) in a 20% hydroacetonic solution of acetone (vol./vol.).

After remaining 2 days in the conditioned environment at 20° C. and 70% R.H., the plants were sprayed on both sides of the leaves with an aqueous suspension of *Helminthosporium teres* (250.000 conidii per cc.). After 24 hours in a humidity saturated atmosphere, at 21° C., the plants were kept in a conditioned environment for the incubation of the fungus.

At the end of this period (12 days), the gravity of infection was estimated by observation, with a scale of indexes ranging from 100 (healthy plant) to 0 (completely infected plant).

The relative data are summarized in Table 1.

TABLE 1

| Compound number | Dosage (ppm) | % Control Helminthosporium |
|---|---|---|
| 1 | 500 | 100 |
|  | 125 | 100 |
| 2 | 500 | 100 |
|  | 125 | 100 |

We claim:

1. A composition suitable for inhibiting the growth of pathogenous fungi in the cultivation of useful plants including at least one benzophenone compound of the formula (I):

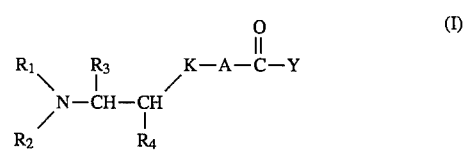

wherein:

$R_1$ and $R_2$, the same or different, represent a $C_1$–$C_6$ alkyl group or a $C_7$–$C_{10}$ arylalkyl group;

or $R_1$ and $R_2$ together with the N atom, represent a $C_3$–$C_8$ heterocyclic group or $C_2$–$C_7$ heterocyclic group containing a second heteroatom selected from O and S, said heterocyclic groups being optionally substituted with one or more $C_1$–$C_4$ alkyl groups;

$R_3$ represents an hydrogen atom or a $C_1$–$C_3$ alkyl group;

$R_4$ represents a $C_1$–$C_3$ alkyl group;

K represents an oxygen atom or methylene;

A represents a benzene group, optionally substituted with one or more halogen atoms, $C_1$–$C_4$ alkyl or haloalkyl groups, $C_1$–$C_4$ alkoxylic or $C_1$–$C_4$ haloalkoxylic groups;

Y represents a $C_6$–$C_{10}$ aryl group, said group being optionally substituted with one or more halogen atoms, $C_1$–$C_4$ alkyl or haloalkyl groups, $C_1$–$C_4$ alkoxylic or haloalkoxylic groups, a fungicidally effective adjuvant or carrier suitable for application to plants, and a surface-active agent selected from the group consisting of sodium, calcium, triethanolamine salts of alkylsulphates, alkylsuphonates, alkyl-aryl sulphonates, polyethoxylated alkylphenols, fatty alcohols condensed with ethylene oxide, polyoxyethylated fatty acids, esters of polyoxyethylated sorbitol, polyoxyethylate fats, and lignin sulphonates.

2. A benzophenone compound having anti-fungal activity useful for treating agricultural products which is 4-[ 3-(3-benzoylphenyl)-2-methyl-3-oxapropyl]-2,6-dimethylmorpholine (cis isomer).

3. A benzophenone compound having an anti-fungal activity useful for treating agricultural products which is N-[3-(3-benzoylphenyl)-2-methyl-3-oxapropyl]-N-benzyl-N-methylamine.

4. A benzophenone compound having anti-fungal activity useful for treating agricultural products which is N-[3-(3-benzoylphenyl)- 2-methylpropyl]-N-methyl-N-(3-phenylpropyl)amine.

5. A composition suitable for inhibiting the growth of pathogenous fungi in the cultivation of useful plants comprising (i) a compound of claim 2, 3 or 4; (ii) a fungicidally effective adjuvant or carrier suitable for application to plants; and (iii) a surface-active agent selected from the group consisting of sodium, calcium, triethanolamine salts or alkylsulphates, alkylsulphonates, alkyl-aryl sulphonates, polyethoxylated alkylphenols, fatty alcohols condensed with ethylene oxide, polyoxyethylated fatty acids, esters of polyoxyethylated sorbitol, polyoxyethylated fats, and lignin sulphonates.

* * * * *